United States Patent
Qu et al.

(10) Patent No.: US 10,662,137 B2
(45) Date of Patent: May 26, 2020

(54) METHOD FOR PREPARING HIGH-PURITY CANNABIDIOL

(71) Applicant: Yantai Hemp Biotechnology Co., Ltd., Yantai (CN)

(72) Inventors: Guiwu Qu, Yantai (CN); Ming Cui, Yantai (CN)

(73) Assignee: Yantai Hemp Biotechnology Co., Ltd., Yantai, Shandong (CN)

( * ) Notice: Subject to any disclaimer, the term of this patent is extended or adjusted under 35 U.S.C. 154(b) by 0 days.

(21) Appl. No.: 16/242,274

(22) Filed: Jan. 8, 2019

(65) Prior Publication Data
US 2019/0210946 A1    Jul. 11, 2019

(30) Foreign Application Priority Data

Jan. 10, 2018 (CN) .......................... 2018 1 0022445

(51) Int. Cl.
| | | |
|---|---|---|
| *C07C 37/84* | (2006.01) | |
| *B01J 20/285* | (2006.01) | |
| *B01D 15/18* | (2006.01) | |
| *B01J 20/28* | (2006.01) | |
| *A61K 31/05* | (2006.01) | |
| *A61K 36/185* | (2006.01) | |
| *C07C 37/00* | (2006.01) | |
| *C07C 37/82* | (2006.01) | |
| *B01D 15/26* | (2006.01) | |

(52) U.S. Cl.
CPC .............. *C07C 37/84* (2013.01); *A61K 31/05* (2013.01); *A61K 36/185* (2013.01); *B01D 15/1864* (2013.01); *B01D 15/1871* (2013.01); *B01D 15/265* (2013.01); *B01J 20/285* (2013.01); *B01J 20/28085* (2013.01); *C07C 37/004* (2013.01); *C07C 37/82* (2013.01); *A61K 2236/00* (2013.01)

(58) Field of Classification Search
CPC ..... C07C 37/84; C07C 37/82; C07C 37/0004; A61K 36/185; A61K 31/05; A61K 2236/00; B01J 20/28025; B01D 15/1871; B01D 15/1864; B01D 15/265
See application file for complete search history.

(56) References Cited

U.S. PATENT DOCUMENTS

| | | | | |
|---|---|---|---|---|
| 2006/0167283 | A1* | 7/2006 | Flockhart ................ | C07C 37/70 549/390 |
| 2018/0362429 | A1* | 12/2018 | Zhang ..................... | C07C 37/82 |

FOREIGN PATENT DOCUMENTS

| | | | | |
|---|---|---|---|---|
| CN | 106511577 | * | 3/2017 | ............. A61K 36/76 |

OTHER PUBLICATIONS

Li et al. ("Development of adsorptive (non-ionic) macroporous resins and their uses in the purification of pharmacologically-active natural products from plant sources", Natural Product Reports, vol. 27, 2010, pp. 1493-1510).*

* cited by examiner

*Primary Examiner* — Rosalynd A Keys
(74) *Attorney, Agent, or Firm* — Garvey, Smith & Nehrbass, Patent Attorneys, L.L.C.; Vanessa M. D'Souza; Seth M. Nehrbass

(57) ABSTRACT

A method for preparing high-purity cannabidiol is characterized in that: the leaves of cannabis and top portions of the plant which account for about one-fifth of the whole plant are used as extraction sites; a technology of combined macroporous adsorption resin chromatography and polyamide chromatography is used for purification; and a mixed solvent system is used for crystallization purification so as to ensure that the yield is improved to the maximum extent under the premise of obtaining a high-purity product. The product obtained from this method contains high-purity CBD; the method has a high yield and is a simple process, and thus easy to industrialize.

4 Claims, 2 Drawing Sheets

METHOD FOR PREPARING HIGH-PURITY CANNABIDIOL

This application claims priority to Chinese patent application number 201810022445.8, filed Jan. 10, 2018, with a title of METHOD FOR PREPARING HIGH-PURITY CANNABIDIOL. The above-mentioned patent application is incorporated herein by reference in its entirety.

TECHNICAL FIELD

The present invention belongs to the field of pharmaceutical and chemical industries, and more particularly relates to a method for preparing high-purity cannabidiol.

BACKGROUND

*Cannabis sativa* Linn. is an annual herb of *Cannabis* Linn., Cannabinaceae, and the flower, leaf and stem products of its mature female plants are called Marijuana. Currently, cannabinoids (CBs) isolated from marijuana plants are of more than 80 kinds, which mainly includes tetrahydrocannabinol (THC), cannabidiol (CBD), cannabinol (CBN), cannabichromene (CBC) and the like, where the contents of THC and CBD are the highest.

THC is one of the important active ingredients in *Cannabis sativa*. It has a good neuroprotective effect and can be used to treat cancer-induced vomiting. However, due to its hallucinogenic effect, only a cannabis variety which has a THC content in flowers and leaves during the growth period of less than 0.3% (i.e. industrial cannabis) is allowed to be planted.

CBD, which was isolated from *Cannabis sativa* in the nineteen forties, is another important active ingredient in *Cannabis sativa*, and is also an important non-addictive active ingredient of *Cannabis sativa*. Through in vivo experiments, it is found that, CBD not only can antagonize the mental activities induced by THC-activated cannabinoid type I receptor (CB1R), but also has anticonvulsive, sedative-hypnotic, anxiolytic, antipsychotic, anti-inflammatory and neuroprotective effects, and is a natural active ingredient that is highly promising in the fields of medicine and food.

It is a premise for the development and application of CBD to remove THC and other ingredients with hallucinogenic and addictive effects as much as possible, so as to obtain a high-purity product. Currently, in publicly available information, there are some reports on methods for extracting CBD from industrial cannabis. For example, CN105505565A and CN105535111A respectively disclose a method for preparing a CBD-enriched cannabis oil or cannabis extract by using a supercritical or subcritical extraction technology; CN107011125A discloses a method for enriching cannabidiol, where the specific process includes two steps, i.e., conducting carbon dioxide supercritical extraction to obtain a preliminary extract of cannabis flowers and leaves, and then performing column chromatography, wherein the medium used for the column chromatography is AB-8, D-101, DA-201, HPD-100, HPD-100A, LSA-10, MCIGEL, DIAION or SEPABEADS, and the like styrene macroporous adsorption resins or silica gels; CN106831353A discloses another method for extracting cannabidiol, where the specific process includes alcohol extraction and water precipitation, column chromatography, crystallization, and the like steps, where the medium used for the column chromatography is AB-8, D-101, XDA-8, LSA-7, D-941, DM-130, ADS-17, SP-825 or HPD-600, and the like macroporous adsorption resins, a MCI resin or an octadecyl bonded silica gel, etc., and the crystallization solvent is ethanol.

The marijuana plant has complex phenolic ingredients and many ingredients with similar polarities. Therefore, even in the case that the ethanol crystallization process of CN106831353A is used to prepare CBD, hallucinogenic or addictive ingredients such as THC can still be detected in the product, which affects the safety of the CBD product.

SUMMARY

To solve the above technical problems, the present invention provides a method for preparing high-purity CBD, wherein the product prepared has CBD purity of more than 98% and THC is only detected in trace amounts, or not detected at all.

In a preferred embodiment of the present invention, the method for preparing the high-purity CBD has a technical solution including the following steps:

(1) Solvent extraction:

In a preferred embodiment of the present invention, the extracted sites of cannabis are sun-dried and pulverized into a coarse powder and extracted three times with 95% ethanol as a solvent, wherein each time the amount of the solvent is 10-20 times the amount of the powder. The extracts are combined and filtered, and dealcoholized under reduced pressure at 50° C. to 70° C., until the solution is slightly cloudy, and then cooled to room temperature.

In a preferred embodiment of the present invention, the extraction sites used for solvent extraction refer to the leaves of cannabis and top portions of the plant which account for about one-fifth of the whole plant.

(2) Combined two-step column chromatography:

In a preferred embodiment of the present invention, the first step of column chromatography uses a macroporous adsorption resin as the chromatographic medium, and the column loading is 3-10 g hemp stems and leaves/mL resin. The hemp stems and leaves are preferably medicinal materials that can be from China. Firstly, the column is eluted with preferably 3-10 column volumes, more preferably 5-10 column volumes, of 45-55% ethanol to wash away most of the highly-polar impurities, and then, it is eluted with 3-5 column volumes of 80-95% ethanol to elute cannabidiol. An eluent rich in the cannabidiol is collected, and dealcoholized under reduced pressure at 50° C. to 70° C., until the solution is slightly cloudy, and then cooled to room temperature.

In a preferred embodiment of the present invention, the aforementioned first step of column chromatography enriches CBD, and the macroporous adsorption resin as adopted includes, but is not limited to, HPD-417, HPD-450, AB-8, ADS-17, D-101, DM-130, LSA-7, and LSA-10.

In a preferred embodiment of the present invention, the second step of column chromatography uses a polyamide adsorption resin as the chromatographic medium, and the column loading is 30-50 mg CBD/mL resin. Firstly, the column is eluted with 3-5 column volumes of 30-50% ethanol to wash away impurities, and then eluted with 3-5 column volumes of 50-80% ethanol to elute cannabidiol. An eluent rich in the cannabidiol is collected, and concentrated under reduced pressure at 50° C. to 70° C. to obtain a thick paste.

(3) Crystallization purification of mixed solvent:

In a preferred embodiment of the present invention, the thick paste is dissolved in a mixed solvent system to prepare a saturated solution of CBD, and the solution is allowed to stand to obtain colorless or pale yellow crystals, which are filtered and dried to obtain high-purity CBD crystals.

In a preferred embodiment of the present invention, the mixed solvent system adopted in the above crystallization is composed of A (cyclohexane or n-hexane) and B (ethanol or methanol) in a ratio of (1-5):1 (V/V).

Both the macroporous adsorption resin chromatography and the polyamide chromatography are separation and purification techniques often used in industrial production, but their principles of separating natural compounds are different, and the separation effects of them can complement each other. The present invention combines the two and obtains a better impurity removal effect.

In a preferred embodiment of the present invention, a mixed solvent is employed as a crystallization solvent for the purpose of adjusting the polarity of the solvent, so as to increase the solubility of impurities such as THC as much as possible while forming a supersaturated solution of CBD to the maximum extent, and to improve the crystallization yield while ensuring the purity of the product.

DETAILED DESCRIPTION

Figure 1:
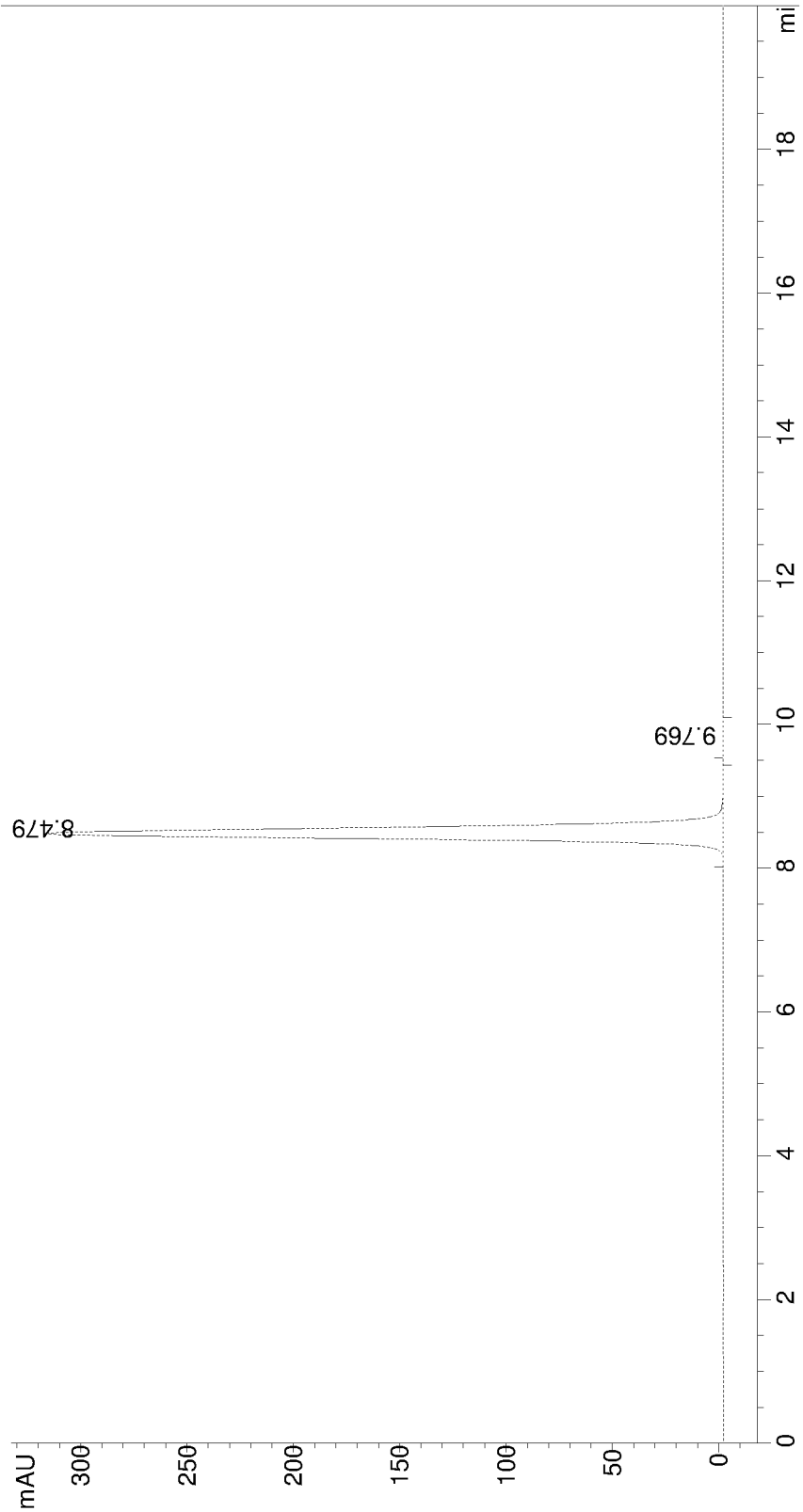
FIG. 1 is a liquid chromatogram of CBD prepared according to the method provided by a preferred embodiment of the present invention.
Figure 2:
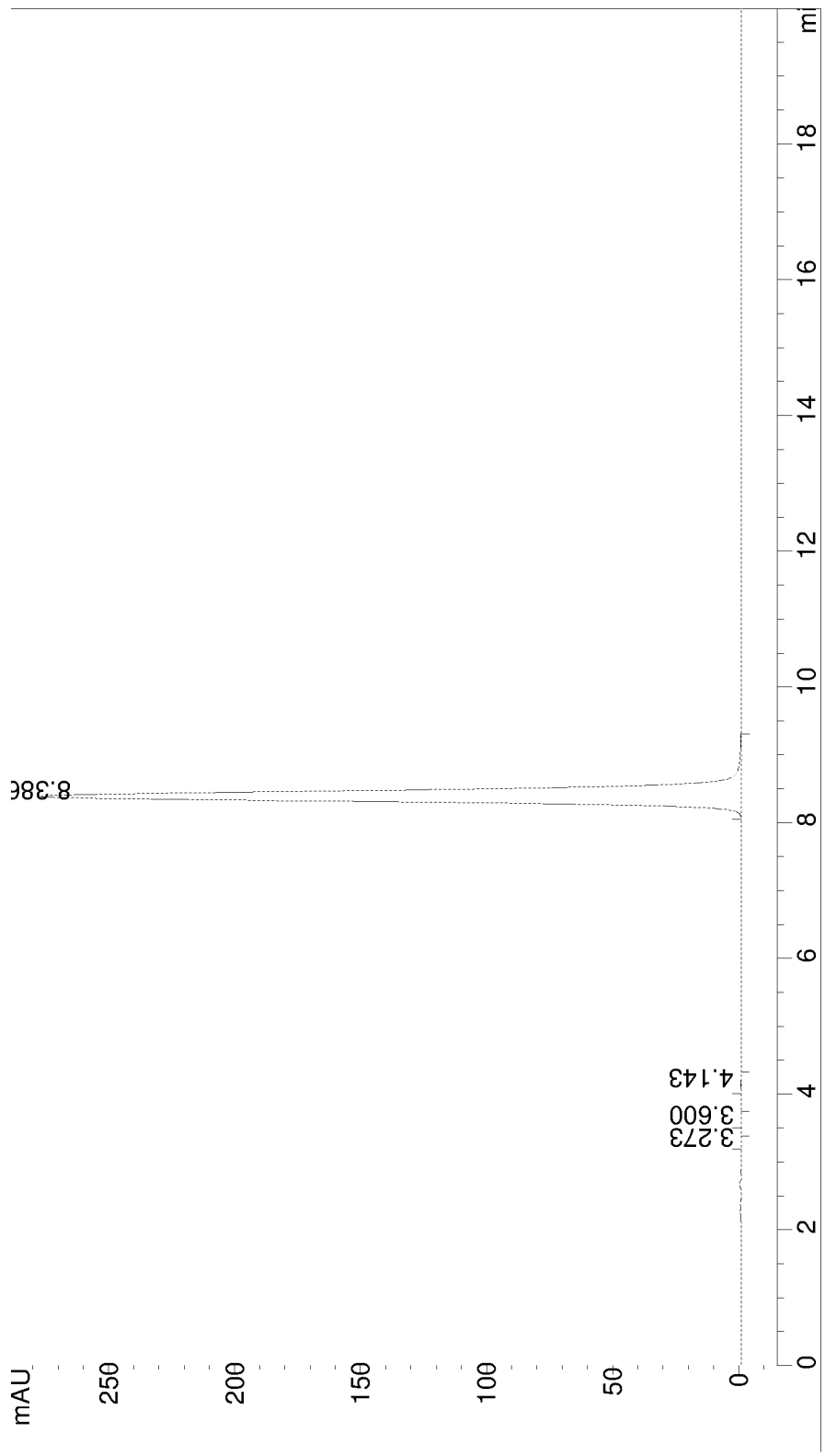
FIG. 2 is a liquid chromatogram of a CBD standard.

The following embodiments are intended to illustrate the present invention, rather than limit the essential scope of the present invention.

Preferred Embodiment 1. Preparation of High-Purity CBD (1) Solvent extraction:
The top portions of cannabis which account for about one-fifth of the whole plant were taken, sun-dried and pulverized into a coarse powder, and extracted three times with 95% ethanol as a solvent, where each time the amount of the solvent was 10 times the amount of the powder. The extracts were combined and filtered, and dealcoholized under reduced pressure at 50° C. until the solution was slightly cloudy, and then cooled to room temperature.

(2) Two-step column chromatography:
The first step of column chromatography: a macroporous adsorption resin of type HPD-417 was used as the chromatographic medium, and the column loading was 5 g hemp stems and leaves/mL resin. Firstly, the column was eluted with 7 column volumes of 45% ethanol to wash away most of the highly-polar impurities, and then eluted with 5 column volumes of 85% ethanol to elute cannabidiol. An eluent rich in the cannabidiol was collected, and dealcoholized under reduced pressure at 50° C. until the solution was slightly cloudy, and then cooled to room temperature.

The second step of column chromatography: a polyamide adsorption resin was used as the chromatographic medium, and the column loading was 30 mg CBD/mL resin. Firstly, the column was eluted with 3 column volumes of 30% ethanol to wash away impurities and then eluted with 3 column volumes of 80% ethanol to elute cannabidiol. An eluent rich in the cannabidiol was collected, and concentrated under reduced pressure at 50° C., to obtain a thick paste.

(3) Crystallization of mixed solvent: the thick paste was dissolved in a mixed solvent system (cyclohexane:ethanol=3:1, V/V) to prepare a saturated solution of CBD, and the solution was allowed to stand to obtain colorless or pale yellow crystals, which were filtered and dried to obtain high-purity CBD crystals.

Preferred Embodiment 2. Preparation of High-Purity CBD (1) Solvent extraction: the top portions of cannabis which account for about one-fifth of the whole plant were taken, sun-dried and pulverized into a coarse powder, and extracted three times with 95% ethanol as a solvent, where each time the amount of the solvent was 15 times the amount of the powder. The extracts were combined and filtered, and dealcoholized under reduced pressure at 60° C. until the solution was slightly cloudy, and then cooled to room temperature.

(2) Two-step column chromatography:
The first step of column chromatography: a macroporous adsorption resin of type HPD-450 was used as the chromatographic medium, and the column loading was 3 g hemp stems and leaves/mL resin. Firstly, the column was eluted with 5 column volumes of 55% ethanol to wash away most of the highly-polar impurities, and then eluted with 3 column volumes of 95% ethanol to elute cannabidiol. An eluent rich in the cannabidiol was collected, and dealcoholized under reduced pressure at 60° C. until the solution was slightly cloudy, and then cooled to room temperature.

The second step of column chromatography: a polyamide adsorption resin was used as the chromatographic medium, and the column loading was 50 mg CBD/mL resin. Firstly, the column was eluted with 3 column volumes of 50% ethanol to wash away impurities and then eluted with 5 column volumes of 75% ethanol to elute cannabidiol. An eluent rich in the cannabidiol was collected, and concentrated under reduced pressure at 60° C., to obtain a thick paste.

(3) Crystallization of mixed solvent: the thick paste was dissolved in a mixed solvent system (n-hexane:methanol=3:1, V/V) to prepare a saturated solution of CBD, and the solution was allowed to stand to obtain colorless or pale yellow crystals, which were filtered and dried to obtain high-purity CBD crystals.

Preferred Embodiment 3. Preparation of High-Purity CBD (1) Solvent extraction: the top portions of cannabis which account for about one-fifth of the whole plant were taken, sun-dried and pulverized into a coarse powder, and extracted three times with 95% ethanol as a solvent, where each time the amount of the solvent was 20 times the amount of the powder. The extracts were combined and filtered, and dealcoholized under reduced pressure at 70° C. until the solution was slightly cloudy, and then cooled to room temperature.

(2) Two-step column chromatography:
The first step of column chromatography: a macroporous adsorption resin of AB-8 type was used as the chromatographic medium, and the column loading was 8 g hemp stems and leaves/mL resin. Firstly, the column was eluted with 3 column volumes of 55% ethanol to wash away most of the highly-polar impurities and then eluted with 3 column volumes of 95% ethanol to elute cannabidiol. An eluent rich in the cannabidiol was collected, and dealcoholized under reduced pressure at 70° C., until the solution was slightly cloudy, and then cooled to room temperature.

The second step of column chromatography: a polyamide adsorption resin was used as the chromatographic medium, and the column loading was 45 mg CBD/mL resin. Firstly, the column was eluted with 5 column volumes of 45% ethanol to wash away impurities and then eluted with 3 column volumes of 80% ethanol to elute cannabidiol. An eluent rich in the cannabidiol was collected, and concentrated under reduced pressure at 70° C., to obtain a thick paste.

(3) Crystallization of mixed solvent: the thick paste was dissolved in a mixed solvent system (n-hexane:ethanol=2:1, V/V) to prepare a saturated solution of CBD, and the solution was allowed to stand to obtain colorless or pale yellow crystals, which were filtered and dried to obtain high-purity CBD crystals.

Preferred Embodiment 4. HPLC Detection of CBD Sample

The detection was conducted according to high performance liquid chromatography (Chinese Pharmacopoeia, Appendix V D, Part II).

Chromatographic conditions and system applicability: octadecyl silane bonded silica was used as a filler; methanol-acetonitrile-water-acetic acid (25:50:25:0.4 by volume) was used as a mobile phase, the detection wavelength was 220 nm, and the number of theoretical plates was not less than 4,000 as calculated by cannabidiol.

Detection method: the appropriate amount of the sample was taken, accurately weighed, and dissolved with the mobile phase and quantificationally diluted into a solution which contained about 0.2 mg of the sample per 1 mL. Twenty μl of the solution was accurately measured and injected into a liquid chromatograph and the chromatogram was recorded; and additionally, a cannabidiol control was taken and detected by the same method. The concentration of cannabidiol was obtained by calculating the peak area according to an external standard method.

Detection result: the content of cannabidiol was 99.25% as calculated on the anhydrous substance.

LISTING OF ACRONYMS AND ABBREVIATIONS

° C. degrees Celsius
CB cannabinoid
CBC cannabichromene
CBD cannabidiol
CBN cannabinol
g gram
HPLC High Performance Liquid Chromatography
mAU milli-Absorbance
mg milligram
min minute
mL milliliter
THC tetrahydrocannabinol
V volume
μl microliter The aforementioned description sets forth preferred specific embodiments of the present invention, and the claimed scope of the present invention is not limited thereto. Equivalent substitutions or modifications can be made by those of skill in the art according to the technical solution and inventive concept of the present invention, without departing from the technical scope disclosed by the present invention. These substitutions or modifications all fall within the claimed scope of the present invention.

What is claimed is:

1. A method for preparing high-purity cannabidiol, comprising the following steps:
    (1) a solvent extraction including extracted sites of *cannabis* sun-dried and pulverized into a coarse powder, and extracted three times with 95% ethanol as a solvent, wherein each time the amount of the solvent is 10-20 times the amount of the powder; the extracts are combined and filtered, and dealcoholized under reduced pressure at 50° C. to 70° C. until a solution which remains is slightly cloudy, and then the solution is cooled to room temperature;
    (2) a combined use of macroporous adsorption resin chromatography and polyamide chromatography including:
    a first step of column chromatography using a macroporous adsorption resin as a chromatographic medium, and a column loading of 3-10 g hemp stems and leaves/mL resin; firstly, the column is eluted with 5-10 column volumes of 45-55% ethanol to wash away most highly-polar impurities and then eluted with 3-5 column volumes of 80-95% ethanol to elute cannabidiol; an eluent rich in the cannabidiol is collected, and dealcoholized under reduced pressure at 50° C. to 70° C. until a solution is slightly cloudy, and then cooled to room temperature;
    a second step of column chromatography using a polyamide adsorption resin as a chromatographic medium, and a column loading is 30-50 mg CBD/mL resin; firstly, the column is eluted with 3-5 column volumes of 30-50% ethanol to wash away impurities and then eluted with 3-5 column volumes of 50-80% ethanol to elute cannabidiol; an eluent rich in the cannabidiol is collected, and concentrated under reduced pressure at 50° C. to 70° C. to obtain a thick paste; and
    (3) a crystallization purification of mixed solvent including the thick paste dissolved in a mixed solvent system to prepare a saturated solution of CBD, and the solution is allowed to stand to obtain colorless or pale yellow crystals, which are filtered and dried to obtain high-purity CBD crystals.

2. The method for preparing high-purity cannabidiol of claim 1, wherein the extracted sites are the leaves of *cannabis* and top portions of the plant which account for about one-fifth of the whole plant.

3. The method for preparing high-purity cannabidiol of claim 1, wherein macroporous adsorption resin chromatography and polyimide chromatography are used in combination, wherein the macroporous adsorption resin as employed comprises, but is not limited to, HPD-417, HPD-450, AB-8, ADS-17, D-101, DM-130, LSA-7, and LSA-10.

4. The method for preparing high-purity cannabidiol of claim 1, wherein a mixed solvent system is used as a crystallization solvent for purification, and the mixed solvent system is composed of A (cyclohexane or n-hexane) and B (ethanol or methanol) in a ratio of (1-5):1 (V/V).

* * * * *